United States Patent [19]

Eichberger et al.

[11] Patent Number: 5,895,815
[45] Date of Patent: Apr. 20, 1999

[54] PROCESS FOR THE PURIFICATION OF 5H-DIBENZ (B,F) AZEPINE

[75] Inventors: Günter Eichberger, Weisskirchen; Walter Raml, Hellmonsödt, both of Austria

[73] Assignee: DSM Chemie Linz GmbH, Austria

[21] Appl. No.: 08/942,489

[22] Filed: Oct. 2, 1997

Related U.S. Application Data

[63] Continuation of application No. 08/577,877, Dec. 22, 1995, abandoned.

[30] Foreign Application Priority Data

Dec. 27, 1994 [AT] Austria ................ 2408/94

[51] Int. Cl.$^6$ ................ C07D 223/22; C07D 223/26
[52] U.S. Cl. ................ 540/588
[58] Field of Search ................ 540/588

[56] References Cited

U.S. PATENT DOCUMENTS

| | | | |
|---|---|---|---|
| 3,016,373 | 1/1962 | Saggiomo et al. | 540/588 |
| 3,074,931 | 1/1963 | Craig | 540/588 |
| 3,449,324 | 6/1969 | Schramek et al. | 540/588 |
| 3,531,466 | 9/1970 | Beschke et al. | 540/588 |

FOREIGN PATENT DOCUMENTS

| | | |
|---|---|---|
| 0237952 A1 | 9/1987 | European Pat. Off. . |
| 0396134 A1 | 11/1990 | European Pat. Off. . |

OTHER PUBLICATIONS

Perry et al., Chemical Engineers' Handbook, Fifth Edition, pp. 17-12 to 17-13, 1983.

Cheronis, Technique of Organic Chemistry, vol. VI, pp. 13-16, 1954.

Furniss et al., Vogel's Textbook of Practical Organic Chemistry, Fourth Edition, pp. 100-120, 1986.

Ullmann's Encyclopedia of Industrial Chemistry, Fifth Edition, pp. 3-41 and 577, 1985.

*Primary Examiner*—Mukund J. Sham
*Assistant Examiner*—Deepak Rao
*Attorney, Agent, or Firm*—Wenderoth, Lind & Ponack, L.L.P.

[57] ABSTRACT

Process for the purification of 5H-dibenz[b,f]a-zepine, which comprises evaporating 5H-dibenz[b, f]azepine under reduced pressure from a reaction mixture obtained by catalytic dehydrogenation of 10,11-dihydro-5H-dibenz-[b,f] azepine in the 1st step and depositing it as a solid, suspending the deposited product in an aromatic hydrocarbon in the 2nd step and then isolating pure 5H-dibenz[b,f]azepine.

4 Claims, No Drawings

PROCESS FOR THE PURIFICATION OF 5H-DIBENZ (B,F) AZEPINE

This application is a continuation of now abandoned application, Ser. No. 08/577,877, filed Dec. 22, 1995.

5 H-Dibenz|b,f|azepine, generally known under the name iminostilbene, is an intermediate for pharmaceutically active substances, such as carbamazepine.

Iminostilbene is prepared by catalytic dehydrogenation of 10,11-dihydro-5H-dibenz|b,f|azepine, known under the name iminodibenzyl. In particular, in the case of catalytic dehydrogenation in the liquid phase or in the melt, as described, for example, in EP 0 237 952 or EP 0 396 134, iminostilbene, however, contains a large number of impurities, such as, for example, a dimerization product of iminostilbene or acridines, which cannot be removed on further processing to give carbamazepine.

The object of the present invention was accordingly to find a suitable process for the purification of iminostilbene, with which an adequately high purity, together with simultaneous avoidance of losses in yield, is guaranteed. Unexpectedly, it was possible to achieve this object by the combination of two purification steps.

The invention relates to a process for the purification of 5H-dibenz|b,f|azepine, which comprises evaporating 5H-dibenz|b,f|azepine under reduced pressure from a reaction mixture obtained by catalytic dehydrogenation of 10,11-dihydro-5H-dibenz|b,f|azepine in the 1st step and depositing it as a solid, suspending the deposited product in an aromatic hydrocarbon in the 2nd step and then isolating pure 5H-dibenz|b,f|azepine.

If iminostilbene is prepared, for example, analogously to EP 0 237 952 or EP 0 396 134, a reaction mixture obtained by catalytic dehydrogenation of 10,11-dihydro-5H-dibenz |b,f|azepine contains 5H-dibenz|b,f|-azepine (iminostilbene) contaminated with, for example, acridines and dimerization products, unreacted 10,11-dihydro-5H-dibenz|b,f|azepine, reacted and excess hydrogen acceptor, a catalyst and optionally a solvent, for example, as mentioned in EP 0 396 134, and one or more high-boiling polar protic solvents, if appropriate in a mixture with one or more apolar solvents.

Before iminostilbene is purified by the process according to the invention, it is advantageous for the reutilizability of the catalyst to filter off the catalyst, as described in EP 0 237 952 and EP 0 396 134, if appropriate by prior dissolution of the melt in a suitable solvent, such as, for example, acetone, chloroform, dimethyl sulfoxide, dimethylformamide and/or one or more alcohols.

In the 1st step of the process according to the invention for the purification of iminostilbene, if appropriate the solvent is first distilled off from the reaction mixture described above, optionally under reduced pressure, for example via a Vigreux column. Iminostilbene is then evaporated under reduced pressure from the reaction mixture which still remains and deposited in solid form, for example by means of a scrape chiller.

The pressure can vary during this process, depending on the composition of the reaction mixture, and is preferably between 10 and 100 mbar.

The temperature can likewise vary, depending on the composition of the reaction mixture, and is preferably between 120 and 260° C.

The product thus obtained is then homogenized in the 2nd step, optionally, for example, by triturating, suspended in an aromatic hydrocarbon, such as, for example, toluene or xylene, preferably in toluene, and stirred for a few minutes, preferably 10 to 20 minutes. The iminostilbene purified in this way is then isolated by filtering off with suction or filtering off, using the same suspending agent as is used in the second purification step, and, if desired, washed with petroleum ether and dried in vacuo at approximately 40–70° C. The mother liquor obtained in this process can be recycled and, for example, employed again as suspending agent in the second purification step.

By means of the process according to the invention, iminostilbene is obtained in high purity, with a content determined by means of gas chromatography of over 99 area %, without interfering impurities and without great losses in yield. The iminostilbene purified in this way is therefore particularly suitable for further processing to give pharmaceutical active compounds, such as carbamazepine.

EXAMPLES 1–3

150 g (0.77 mol) of 10,11-dihydro-5H-dibenz|-b,f| azepine, 100 ml (0.85 mol) of o-nitrotoluene, 9 ml of a solvent (Table 1) and 9 g of 5% Pd/C were initially introduced into a 500 ml four-necked round-bottomed flask, and the flask was flushed with $N_2$ and heated to 235° C. in the course of 20–25 minutes. After approximately 2 hours, the course of the reaction was monitored by means of GC, the reaction mixture was diluted at 235–240° C. with 100 ml of o-nitrotoluene and the catalyst was filtered off with suction.

The solvent and excess nitrotoluene were then distilled off at a pressure between 90 and 30 mbar. The head temperature was between 150 and 170° C. and the bottom temperature between 150 and 219° C. Iminostilbene was then evaporated at a pressure between 30 and 15 mbar and deposited as a solid. The head temperature in this case was between 180 and 219° C. and the bottom temperature between 216 and 240° C.

The solid thus obtained was comminuted in a mortar, suspended in 100 ml of toluene and stirred for 15 minutes. The product was then filtered off with suction, washed with 20 ml of toluene and 50 ml of petroleum ether and dried at 60° C. in vacuo.

Table 1 indicates the yields which were obtained without recycling the mother liquor, as well as the solvents of the different experiments and the content of impurities. The values were determined here by means of GC (gas chromatography).

TABLE 1

| Ex. | Solvent | Yield | A% | A% IDS | A% acridine | A% toluidine |
|---|---|---|---|---|---|---|
| 1 | Diethylene glycol | 117 g (78.8%) | 99.5 | 0.1 | 0.1 | 0.1 |
| 2 | Diethylene glycol monoethyl ether | 116.6 g (78.5%) | 98.8 | 0.9 | <0.1 | <0.1 |
| 3 | Polyethylene glycol 400 | 119.4 g (80.4%) | 99.6 | 0.2 | <0.1 | <0.1 |

A% Area per cent determined using GC IDB Iminodibenzyl

What we claim is:

1. A process for the purification of 5H-dibenz|b,f|azepine, which consists essentially of evaporating 5H-dibenz|b,f| azepine under reduced pressure from a reaction mixture obtained by catalytic dehydrogenation of 10,11-dihydro-5H-dibenz|b,f|azepine in the 1st step and depositing it as a solid, suspending the deposited product in an aromatic hydrocarbon in the 2nd step and then isolating pure 5H-dibenz|b,f| azepine.

2. The process as claimed in claim 1, wherein the lot step is carried out at a temperature of 120–260° C.

3. The process as claimed in claim 1, wherein the 1st step is carried out at a pressure between 10 and 100 mbar.

4. The process as claimed in claim 1, wherein the deposited product is suspended in toluene.

* * * * *